(12) United States Patent
Shrikant

(10) Patent No.: US 11,266,691 B2
(45) Date of Patent: Mar. 8, 2022

(54) METHODS AND MATERIALS FOR PRODUCING T CELLS

(71) Applicant: Mayo Foundation for Medical Education and Research, Rochester, MN (US)

(72) Inventor: Protul Shrikant, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/851,926

(22) Filed: Apr. 17, 2020

(65) Prior Publication Data
US 2020/0237826 A1    Jul. 30, 2020

Related U.S. Application Data

(62) Division of application No. 15/746,062, filed as application No. PCT/US2016/042077 on Jul. 13, 2016, now Pat. No. 10,624,925.

(60) Provisional application No. 62/194,722, filed on Jul. 20, 2015.

(51) Int. Cl.
| | |
|---|---|
| *A61K 35/17* | (2015.01) |
| *C12N 5/0783* | (2010.01) |
| *A61K 39/00* | (2006.01) |
| *G01N 33/50* | (2006.01) |

(52) U.S. Cl.
CPC .......... *A61K 35/17* (2013.01); *A61K 39/0011* (2013.01); *C12N 5/0636* (2013.01); *G01N 33/505* (2013.01); *A01K 2207/12* (2013.01); *A61K 2039/545* (2013.01); *C12N 2500/34* (2013.01); *C12N 2500/38* (2013.01); *C12N 2501/2302* (2013.01); *C12N 2501/2312* (2013.01)

(58) Field of Classification Search
CPC .............................. A61K 35/17; C12N 5/0636
See application file for complete search history.

(56) References Cited

U.S. PATENT DOCUMENTS

| | | |
|---|---|---|
| 8,192,951 B2 | 6/2012 | Wang et al. |
| 2010/0196311 A1 | 8/2010 | Kim et al. |
| 2018/0064712 A1 | 3/2018 | Pearce et al. |

FOREIGN PATENT DOCUMENTS

| | | |
|---|---|---|
| WO | WO 1990/013629 | 11/1990 |
| WO | WO 2010/151517 | 12/2010 |

OTHER PUBLICATIONS

BD Biosciences, "DimerX I: Recombinant Soluble Dimeric Mouse H-2K[b]:lg Fusion Protein," Technical Data Sheet Cat. No. 550750, © 2008, retrieved on Sep. 18, 2018, URL: <http://www.bdbiosciences.com/ds/pm/tds/550750.pdf>, 3 pages.
Blagih et al., "The Energy Sensor AMPK Regulates T Cell Metabolic Adaptation and Effector Responses In Vivo," Immunity, 42(1):41-54, Jan. 2015.
Cham et al., "Glucose availability regulates 1FN-gamma production and p70S6 kinase activation in CD8+ effector T Cells," J Immunol, Apr. 2005, 174(8): 4670-4677.
Chang et al., "Posttranscriptional control of T cell effector function by aerobic glycolysis," Cell, 153(6):1239-51, Jun. 2013.
Curtsinger et al., "Autodrine IFN-y promots naïve CD8 T cell differentiation and synergizes with IFN-a to stimulate strong function," J Immunol, Jul. 2012, 189(2): 659-668.
European Search Report in European Application No. 16828255.6 dated Dec. 14, 2018, 144 pages.
Extended European Search Report European Application No. 16828255.6 dated Mar. 7, 2019, 295 pages.
Gebhardt et al., "Memory T cells in nonlymphoid tissue that provide enhanced local immunity during infection with herpes simplex virus," Nat Immunol, 2009, 10: 524-530.
Gerriets and Rathmell, "Metabolic pathways in T cell fate and function," Trends in immunology, 33(4):168-173, Apr. 2012.
Gubser et al., "Rapid effector function of memory CD8+ T cells requires an immediate-early glycolytic switch", Nat. Immunol., 14(10):1064-1072, Aug. 2013.
Jacobs et al., "Glucose uptake is limiting in T cell activation and requires CD28-mediated Akt-dependent and independent pathways," J Immunol, Apr. 1, 2008, 180(7): 4476-4486.
Jameson and Masopust, ""Diversity in T Cell Memory: An Embarrassment of Riches,"" Immunity, 2009, 31:859-871.
Jones and Thompson "Revving the engine: signal transduction fuels T cell activation." Immunity, 27(2):173-178, Aug. 2007.
MacIver et al., "Glucose metabolism in lymphocytes is a regulated process with significant effects on imnune cell function and survival," Journal of leukocyte biology, 84(4):949-957, Oct. 2008.
Masopust et al., "Preferential localization of effector memory cells in nonlymphoid tissue," Science, Mar. 2001, 291: 2413-2417.
Mueller et al., "Memory T cell subsets, migration patterns, and tissue residence," Ann. Rev. Immunol., 2013, 31: 137-161.
Palmer et al., "Glucose metabolism regulates T cell activation, differentiation, and functions" Front. Immunol., 6(1), Jan. 2015.
PCT International Preliminary Report on Patentability in International Appln. No. PCT/2016/042077, dated Jan. 23, 2018, 6 pages.
PCT International Search Report and Written Opinion in International Appln. No. PCT/2016/042077, dated Oct. 7, 2016.
R&D Systems, "Recombinant Mouse B7-1/CD80 Fc Chimera," Data sheet for Cat. No. 740-B1, last revised Feb. 2018, retrieved on Sep. 18, 2018, URL <https://resources.rndsystems.com/pdfs/datasheets/740-b1.pdf>, 1 page.
Schenkel et al., "Resident memory CD8 T cells trigger protective innate and adaptive immune responses," Science, 2014, 346: 98-101.
Sukumar and Gattinoni, "The short and sweet of T-cell therapy," Oncoimmunology, Jan. 2014, 3: e27573-1.
Sukumar et al, "Inhibiting glycolytic metabolism enhances CD8+ T cell memory and antitumor formation," J Clin Inv, Oct. 2013, 123(10): 4479-4488.

(Continued)

*Primary Examiner* — Robert C Hayes
(74) *Attorney, Agent, or Firm* — Fish & Richardson P.C.

(57) ABSTRACT

This document provides methods and materials for producing CD8+ T cells. For example, methods and materials for using low glucose levels (e.g., from about 0.3 mM to about 0.7 mM glucose) to culture cells to produce particular populations of T cells (e.g., CD8+ T cells such as tissue resident memory T cells) are provided.

1 Claim, 9 Drawing Sheets

Specification includes a Sequence Listing.

(56) References Cited

OTHER PUBLICATIONS

ThermoFisher [online], Sulfate Latex Beads, 4% w/v, 5 μm, Catalog No. S37227, retrived on Sep. 19, 2018, URL <https://www.thermofisher.com/order/catalog/product/S37227>, 3 pages.

Topham et al., "Tissue-Resident Memory CD8+ T Cells: From Phenotype to Function," Frontiers in immunology, 9:515, Mar. 2018.

CA Office Action in Canadian Appln. No. 2,992,991, dated Feb. 19, 2020, 4 pages.

Medeiros-Silva et al., "CD4 and CD8 T cells participate in the immune memory response against Vaccinia virus after a previous natural infection," Results Immunology, 2013, 3:104-113.

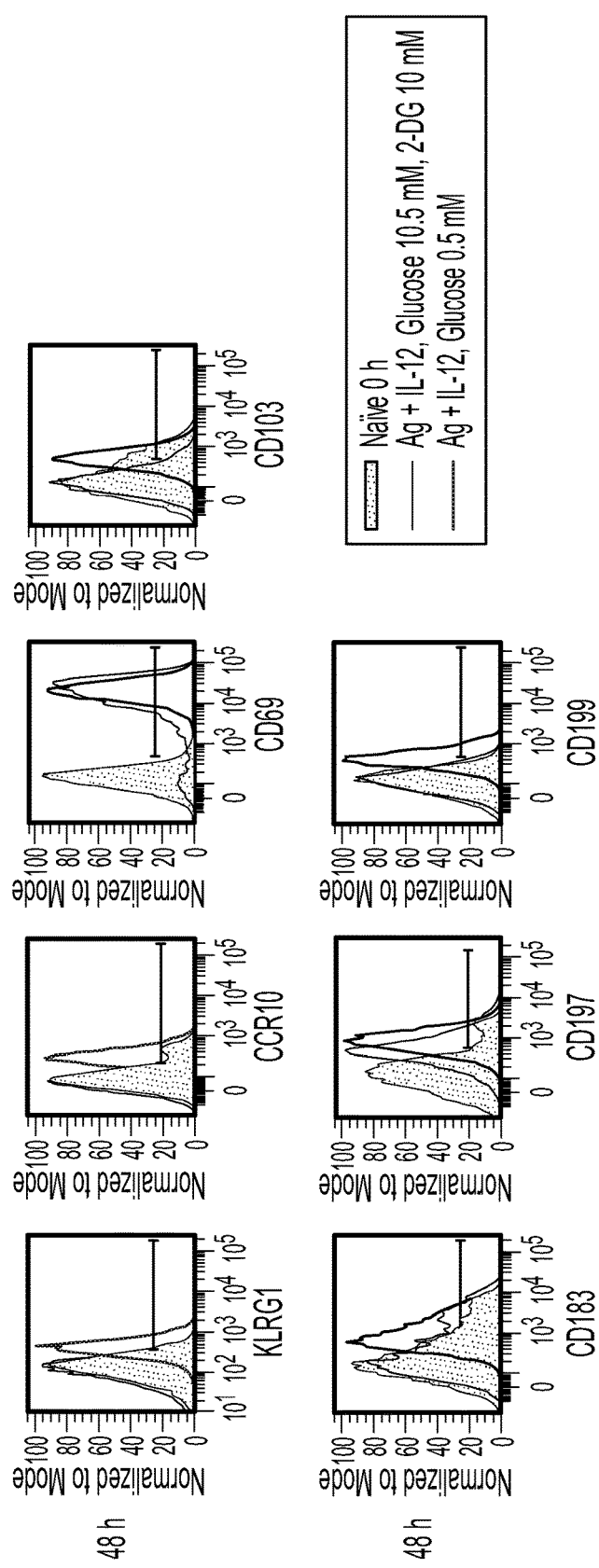

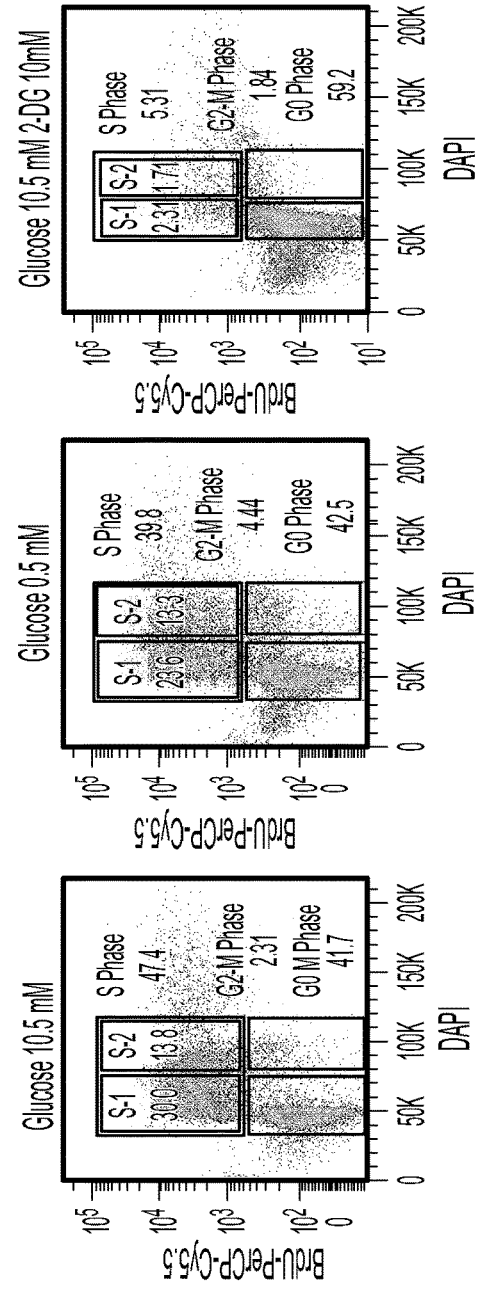
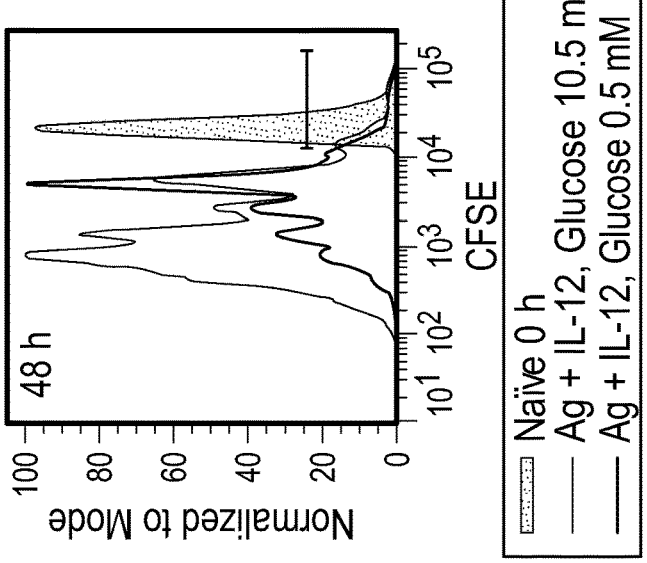
FIG. 2A
FIG. 2B
FIG. 2C

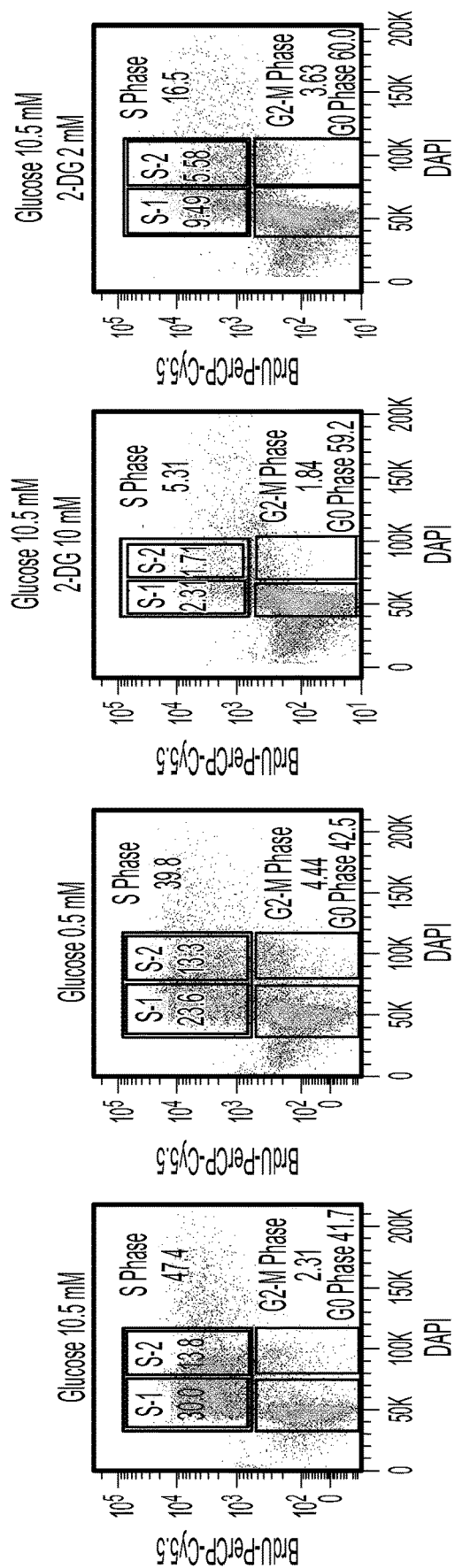
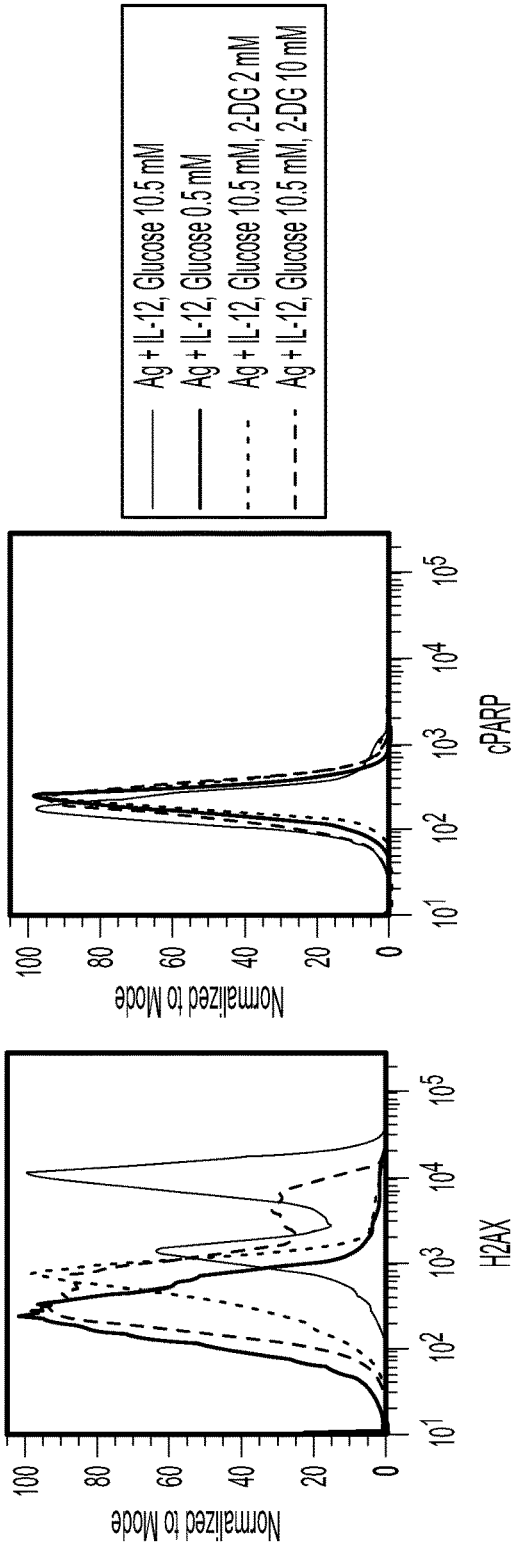
FIG. 3A
FIG. 3B

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: synthetic derived from chicken

<400> SEQUENCE: 1

Ser Ile Ile Asn Phe Glu Lys Leu
1               5
```

US 11,266,691 B2

METHODS AND MATERIALS FOR PRODUCING T CELLS

CROSS-REFERENCE TO RELATED APPLICATIONS

This application is a divisional of U.S. application Ser. No. 15/746,062, filed Jan. 19, 2018 (now U.S. Pat. No. 10,624,925), which is a National Stage application under 35 U.S.C. § 371 of International Application No. PCT/US2016/042077, having an International Filing Date of Jul. 13, 2016, which claims priority to U.S. Application Ser. No. 62/194,722, filed on Jul. 20, 2015. The disclosures of the prior are applications are considered part of the disclosure of this application, and are incorporated in their entirety into this application.

BACKGROUND

1. Technical Field

This document relates to methods and materials for producing CD8+ T cells. For example, this document provides methods and materials for using low glucose levels to culture cells to produce populations of CD8+ T cells (e.g., CD8+ tissue resident memory T cells) that exhibit tertiary tissue residence, effector functions, and/or extended lifespan after transferred into a syngeneic recipient.

2. Background Information

Immunologic memory relates to the immune system's ability to maintain cells that recognize antigen presented in the primary challenge and generate a more rapid and effective immune response upon a second encounter with the same antigen (e.g., after vaccination) to which the individual has previously been exposed. Memory T cells are commonly characterized as long-lived cells that express a different set of surface markers and respond to antigen with less stringent requirements for activation than do naive T cells. The memory T cell population is generally divided into effector memory ($T_{EM}$) and central memory ($T_{CM}$) T cells. A distinct type of memory CD8+ T cells, namely the tissue resident memory T cells ($T_{RM}$), was identified and found to have a unique molecular and functional signature (Masopust et al., *Science*, 291:2413-2417 (2001); Jameson and Masopust, *Immunity*, 31:859-871 (2009); and Mueller et al., *Ann. Rev. Immunol.*, 31:137-161 (2013)). These cells migrate to epithelial tissues where they protect barrier surfaces by immediate effector functions and recruit $T_{CM}$ and $T_{EM}$ cells as well as innate immune cells to generate a systemic response to the challenge. $T_{RM}$ can provide protection against viruses and bacterial challenges and act as sentinels that recruit $T_{CM}$ or $T_{EM}$ CD8+ T cells for immune protection (Gebhardt et al., *Nat. Immunol.*, 10:524-530 (2009); and Schenkel et al., *Science*, 346:98-101 (2014)).

SUMMARY

This document provides methods and materials for producing T cells (e.g., resident memory CD8+ T cells). For example, this document provides methods and materials for using low glucose levels (e.g., between from about 0.3 mM to about 0.7 mM D-glucose or about 0.5 mM D-glucose) in culture media during an initial activation of naïve and/or resting (e.g., CD62hi) CD8+ T cells with antigen and co-stimulation (e.g., B7.1 plus IL-12 at 2-20 ng/mL) to produce a particular functional phenotype of T cells (e.g., tissue resident memory CD8+ T cells). As described herein, T cells (e.g., naïve/resting CD8+ T cells) can be stimulated in culture with one or more antigens of interest in the presence of co-stimulation and from about 0.3 mM to about 0.7 mM glucose (e.g., about 0.5 mM glucose) to generate a population of T cells with specificity towards the one or more antigens of interest. The primed T cells can express markers characteristic of $T_{RM}$ cells such as CD69, KLRG1, VLA-1, CD103, CD183, CD197, and CD199. In addition, the primed T cells can express increased levels of IFNγ and granzyme B (GrB). Once obtained, the primed T cells (e.g., antigen primed $T_{RM}$) can be used in adoptive cellular therapies to treat infections and/or cancer.

In general, one aspect of this document features a method for producing a CD8+ T cell population. The method comprises, or consists essentially of, culturing a first CD8+ T cell population in the presence of from about 0.3 mM to about 0.7 mM glucose for a period of time of at least 48 hours to form a second CD8+ T cell population, wherein CD8+ T cells of the second CD8+ T cell population express CD69, KLRG1, VLA1, CD103, CD183, CD197, CD199, IFNγ, and GrB polypeptides. The T cells of the first CD8+ T cell population can be naïve CD8+ T cells. The first CD8+ T cell population can be cultured in the presence of from about 0.4 mM to about 0.6 mM glucose. The first CD8+ T cell population can be cultured in the presence of about 0.5 mM glucose. The first CD8+ T cell population can be cultured in the presence of an antigen preparation. The CD8+ T cells of the second CD8+ T cell population can be reactive against an antigen of the antigen preparation. The first CD8+ T cell population can be cultured in the presence of IL-12, B7.1, IL-2, or combinations thereof.

In another aspect, this document features a method for producing a CD8+ T cell population. The method comprises, or consists essentially of, culturing a first CD8+ T cell population in the presence of from about 2.5 mM to about 12.5 mM galactose with less than about 0.1 mM of glucose for a period of time of at least 48 hours to form a second CD8+ T cell population, wherein CD8+ T cells of the second CD8+ T cell population express CD69, KLRG1, VLA1, CD103, CD183, CD197, CD199, IFNγ, and GrB polypeptides. The CD8+ T cells of the first CD8+ T cell population can be nave CD8+ T cells. The first CD8+ T cell population can be cultured in the presence of from about 2.5 mM to about 10.5 mM galactose. The first CD8+ T cell population can be cultured in the presence of about 10 mM glucose galactose. The first CD8+ T cell population can be cultured in the presence of an antigen preparation. The CD8+ T cells of the second CD8+ T cell population can be reactive against an antigen of the antigen preparation. The first CD8+ T cell population can be cultured in the presence of IL-12, B7.1, IL-2, or combinations thereof. The first CD8+ T cell population can be cultured in the presence of no glucose.

In another aspect, this document features a method of providing a mammal with CD8+ T cells having the ability to home to tissue within the mammal. The method comprises, or consists essentially of, administering a population of CD8+ T cells produced in culture using from about 0.3 mM to about 0.7 mM glucose, wherein at least a portion of the population CD8+ T cells travel to lymph node, spleen, lung, and liver tissue within the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF THE DRAWINGS

FIGS. 1A-1C. The effect of limiting glucose metabolism during in vitro priming of OT-1 CD8+ T cells on their $T_{RM}$-like surface phenotype. Lowering glucose catabolism by providing 0.5 mM of D-glucose in the culture media (A), but not by blocking glucose catabolism with 2-DG (B), results in the acquisition of $T_{RM}$-like phenotype. Percentages of cells positive for a given $T_{RM}$ marker and the MFI level of $T_{RM}$'S expression are shown (C).

FIGS. 2A-2C. Expansion of OT-1 CD8+ T cells primed in vitro is arrested after initial divisions (A), and numbers of cells surviving a 48-hour culture are 3-4 times lower with 0.5 mM of D-glucose than 10.5 D-glucose in the media during culture with antigen and co-stimulation (B). Proliferation and cell cycle analysis indicates that T cells cultured with 0.5 mM of D-glucose proliferate at a slower rate than T cells cultured under normal (10.5 mM) glucose, whereas the presence of 2-DG blocks their proliferation in response to antigen stimulation (C).

FIGS. 3A-3B. Proliferation and cell cycle analysis (A) and DNA damage and apoptosis (B) of CD8+ T cells primed with antigen and co-stimulated in 48-hour cultures with the indicated media supplements.

DETAILED DESCRIPTION

Figure 1A:
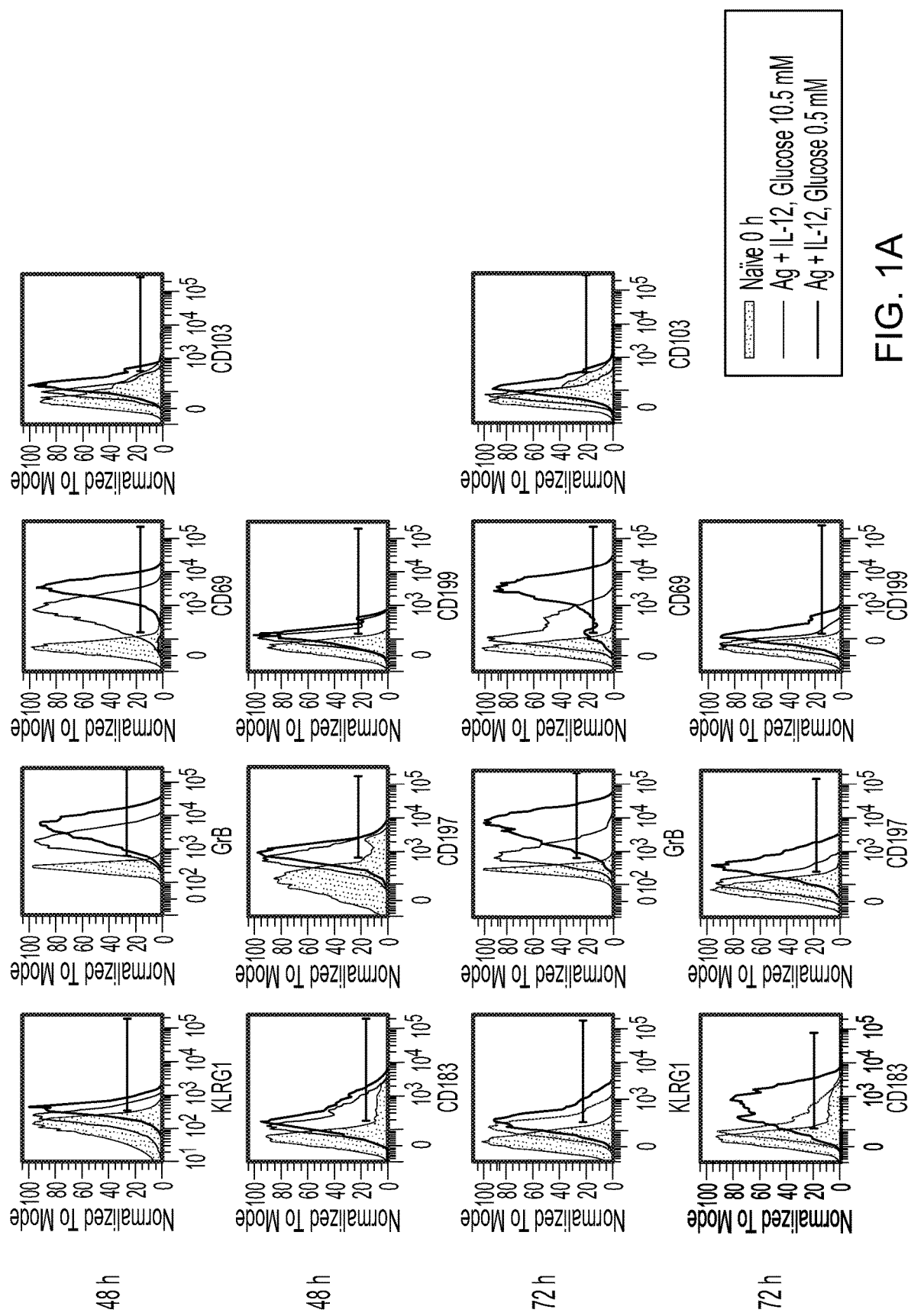

This document provides methods and materials for producing T cells (e.g., resident memory CD8+ T cells). For example, this document provides methods and materials for using low glucose levels (e.g., between from about 0.3 mM to about 0.7 mM glucose) in culture media during an initial activation of naïve and/or resting (e.g., CD62hi) CD8+ T cells with antigen and co-stimulation (e.g., B7.1 plus IL-12 at 2-20 ng/mL) to produce a particular functional phenotype of T cells (e.g., tissue resident memory CD8+ T cells). Examples of such low levels of glucose include those levels that are between about 0.3 mM and about 0.7 mM of glucose (e.g., between about 0.4 mM and about 0.6 mM of glucose or about 0.5 mM). In some cases, the culture can include very little or no glucose and between about 5 mM and about 10.5 mM of galactose. For example, a T cell population can be cultured in the presence of about 7.5 mM of galactose with less than about 0.01 mM of glucose. In some cases, a T cell population can be cultured in the presence of from about 5.0 mM to about 10.5 mM of galactose with less than about 10.5 mM of glucose (e.g., less than about 5 mM, 2.5 mM, or 0.5 mM of glucose).

Any appropriate population of CD8+ T cells can be cultured as described herein to produce a population of T cells having a $T_{RM}$-like surface phenotype. For example, nave or resting (e.g., CD62hi) CD8+ T cells or antigen experienced CD8+ T cells obtained from, for example, lymph nodes, spleen, blood, or bone-marrow can be cultured as described herein to produce a population of CD8+ T cells having a $T_{RM}$-like surface phenotype. CD8+ T cells have a $T_{RM}$-like phenotype when they express CD69, KLRG1, VLA1, CD103, CD183, CD197, CD199, IFNγ, and Granzyme B polypeptides. For example, CD8+ T cells can have a $T_{RM}$-like phenotype when they express CD69, CD103, CD183, CD197, CD199, and KLRG1 as set forth in FIG. 4 for cells cultured with 0.5 mM of glucose.

Any appropriate method can be used to identify CD8+ T cells having a $T_{RM}$-like phenotype. For example, FACS analyses, ELISA, and other antibody-based assays can be used to identify T cells having a $T_{RM}$-like phenotype.

In some cases, CD8+ T cells can be cultured in low levels of glucose (or galactose) as described herein and in a manner designed to stimulate CD8+ T cells reactive against particular antigens of interest. For example, CD8+ T cells can be cultured in the presence of one or more antigens of interest, one or more agents designed to stimulate CD8+ T cells (e.g., co-stimulation agents such as B7.1 plus IL-12 at 2-20 ng/mL), and either from about 0.3 mM to about 0.7 mM of glucose or from about 5 mM and about 10.5 mM of galactose with less than about 0.01 mM of glucose. Any appropriate antigen can be used as described herein to produce a population of CD8+ T cells that have a $T_{RM}$-like phenotype and are reactive against that antigen. For example, bacterial antigens, fungal antigens, parasite antigens, or antigens expressed by cancer cells (e.g., NY-ESO1, WT1, IGFB4, MUC1, TRP2, MelanA, or gp100) can be used. In some cases, the antigens can be expressed by melanoma cancer cells, ovarian cancer cells, lung cancer cells, lymphoma cells, or renal cancer cells. Examples of agents designed to stimulate CD8+ T cells include, without limitation, B7.1, IL-2, IL-12, antigen, IFNα, IFNβ, B7, 4-1BB, and CD40. In some cases, IL-12 and IL-2 are used in combination with antigen plus B7.1 to stimulate CD8+ T cells.

In some cases, CD8+ T cells can be cultured as described herein for an appropriate length of time to result in CD8+ T cells that have a $T_{RM}$-like phenotype and are reactive against an antigen of interest. For example, CD8+ T cells can be cultured in low levels of glucose (or a level of galactose such as a level between about 5 mM and 10.5 mM) as described herein and in a manner designed to stimulate CD8+ T cells reactive against particular antigens of interest between about 48 hours and about 96 hours.

Once a population of CD8+ T cells (e.g., CD8+ T cells that have a $T_{RM}$-like phenotype and are reactive against an antigen of interest) is obtained, the cells can be administered to a mammal for use in, for example, adoptive cellular therapies to treat infections and/or cancer. Any appropriate mammal can be treated with the CD8+ T cells provided herein. For example, humans, horses, cattle, pigs, dogs, cats, mice, and rats can be treated with a population of CD8+ T cells that have a $T_{RM}$-like phenotype and are reactive against an antigen of interest. In some cases, any appropriate number of CD8+ T cells provided herein can be administered to a mammal. For example, between about $1 \times 10^3$ cells and about $1 \times 10^9$ cells can be administered to a mammal. Any appropriate route of administration can be used to administer the CD8+ T cells provided herein to a mammal. For example, CD8+ T cells that have a $T_{RM}$-like phenotype and are reactive against an antigen of interest can be administered intravenously, intra-peritoneally, subcutaneously, intranasally, intramuscularly, intrahepatically, or intranodally.

In some cases, a population of CD8$^+$ T cells (e.g., T cells that have a $T_{RM}$-like phenotype and are reactive against an antigen of interest) can be expanded prior to being administered to a mammal. For example, CD8$^+$ T cells that have a $T_{RM}$-like phenotype and are reactive against an antigen of interest can be expanded by further antigen stimulation with low glucose levels (e.g., about 0.5 mM) and appropriate doses of galactose (e.g., between about 5 mM and 10.5 mM) and/or with antigen in the presence of homeostatic cytokines such as IL-7, IL-15, and/or growth factors such as TGF-β, IFNα, IFNβ, Oncostatin M, and IL-33.

In some cases, CD8$^+$ T cells (e.g., T cells that have a $T_{RM}$-like phenotype) can be produced using low glucose levels (e.g., from about 0.3 mM to about 0.7 mM of glucose) and glutamine (e.g., from about 0.5 mM to about 15 mM of glutamine) in culture media during an initial activation of nave and/or resting (e.g., CD62hi) CD8$^+$ T cells with antigen and co-stimulation (e.g., B7.1 plus IL-12 at 2-20 ng/mL) to produce a particular functional phenotype of CD8$^+$ T cells. For example, naïve and/or resting (e.g., CD62hi) CD8$^+$ T cells can be cultured with low glucose levels (e.g., from about 0.3 mM to about 0.7 mM of glucose) and from about 1.5 mM to about 2.5 mM glutamine during an initial activation with antigen and co-stimulation to produce CD8$^+$ T cells that have a $T_{RM}$-like phenotype. Such cells can be termed glutamine #1 cells. In some cases, naïve and/or resting (e.g., CD62hi) CD8$^+$ T cells can be cultured with low glucose levels (e.g., from about 0.3 mM to about 0.7 mM of glucose) and from about 7.5 mM to about 8.5 mM glutamine during an initial activation with antigen and co-stimulation to produce CD8$^+$ T cells that have a $T_{RM}$-like phenotype. Such cells can be termed glutamine #2 cells. The glutamine #1 cells and glutamine #2 cells can express similar surface markers, but can have different functional properties.

The invention will be further described in the following examples, which do not limit the scope of the invention described in the claims.

EXAMPLES

Example 1—Generating $T_{RM}$ Cells

Lymph node CD8$^+$ T cells (OT-1 PL Rag$^{-/-}$) obtained from TCR transgenic mice were stimulated in vitro with an antigen-presenting construct in the presence of IL-12 (2 ng/mL; Peprotech, Inc.) for 48 to 72 hours. The antigen-presenting construct included sulfate latex microspheres (Life Technologies, Cat. No. 537227) immobilized with DimerX I (a recombinant dimeric mouse H-2K$^b$:Ig fusion protein obtained from BD Biosciences; Cat. No. 550750) and a recombinant mouse B7-1/CD80 Fc chimeric protein (R&D Systems, Cat. No. 740-B1). A short synthetic peptide (SIINFEKL; SEQ ID NO:1; a sequence derived from a chicken ovalbumin polypeptide), which was a cognate antigen for the CD8$^+$ T cells derived from OT-1 PL Rag$^{-/-}$ TCR transgenic mice, was bound to H-2K$^b$ molecules of the antigenic construct at 10 nM concentration. The CD8$^+$ T cells were stimulated with the cognate antigen plus B7.1 in the following culture medium: glucose- and glutamine-free RPMI supplemented with FBS (10%), HEPES (10 mM), NEAA (1 mM), sodium pyruvate (1 mM), glutamine (2 mM), 2-mercaptoethanol (50 μM), and Pen/Strep. This was a low-glucose (LG) medium with the glucose concentration being 0.5 mM. This glucose content came from the 10% FBS. A control culture medium with normal glucose (NG) concentration of 10.5 mM was made from RPMI with 10 mM glucose being added along with the same supplements used to make the LG medium.

The cells were cultured in flat-bottom 96-well plates at $2 \times 10^5/0.2$ mL/well with microspheres at the ratio of 5:1 for various time points. The cell surface phenotype was assessed by flow cytometry analysis at 48 and 72 hours post-stimulation.

CD8$^+$ T cells primed with antigen under low glucose concentration (0.5 mM) expressed surface markers typical of $T_{RM}$: high CD69, KLRG1, VLA1, CD103, CD183, CD197, and CD199 (FIGS. 1A and 1C). The cells also exhibited increased levels of IFNγ and granzyme B (GrB), which is typical for cells with effector cytotoxic and $T_{RM}$ functions. The phenotypic characteristics of $T_{RM}$-like cells were more prominent at 72 hours than at 48 hours from the onset of culture, at which time point the difference between CD8$^+$ T cells cultured under low (0.5 mM) vs. normal (10.5 mM) glucose concentration was more pronounced. The observed changes in CD8$^+$ surface and functional phenotype under low glucose stimulation conditions were not due to blockage in glycolysis since blocked glucose metabolism with 2-DG (2-deoxyglucose) led to activation (upregulated CD69 expression) without acquisition of a $T_{RM}$-like phenotype (FIG. 1B).

Furthermore, CD8$^+$ T cells activated in low glucose culture conditions increased their size and granularity, and underwent limited proliferation for clonal expansion (FIGS. 2A and B), which is in contrast to the effects observed with cells exposed to the 2-DG-containing culture media (FIG. 2C).

These results and the results from FIGS. 3A and 3B demonstrate that T cells can be primed in vitro in the presence of between about 0.3 mM and about 0.7 mM of glucose to produce T cells that have a $T_{RM}$-like phenotype and that are reactive against desired antigens.

Figure 4:
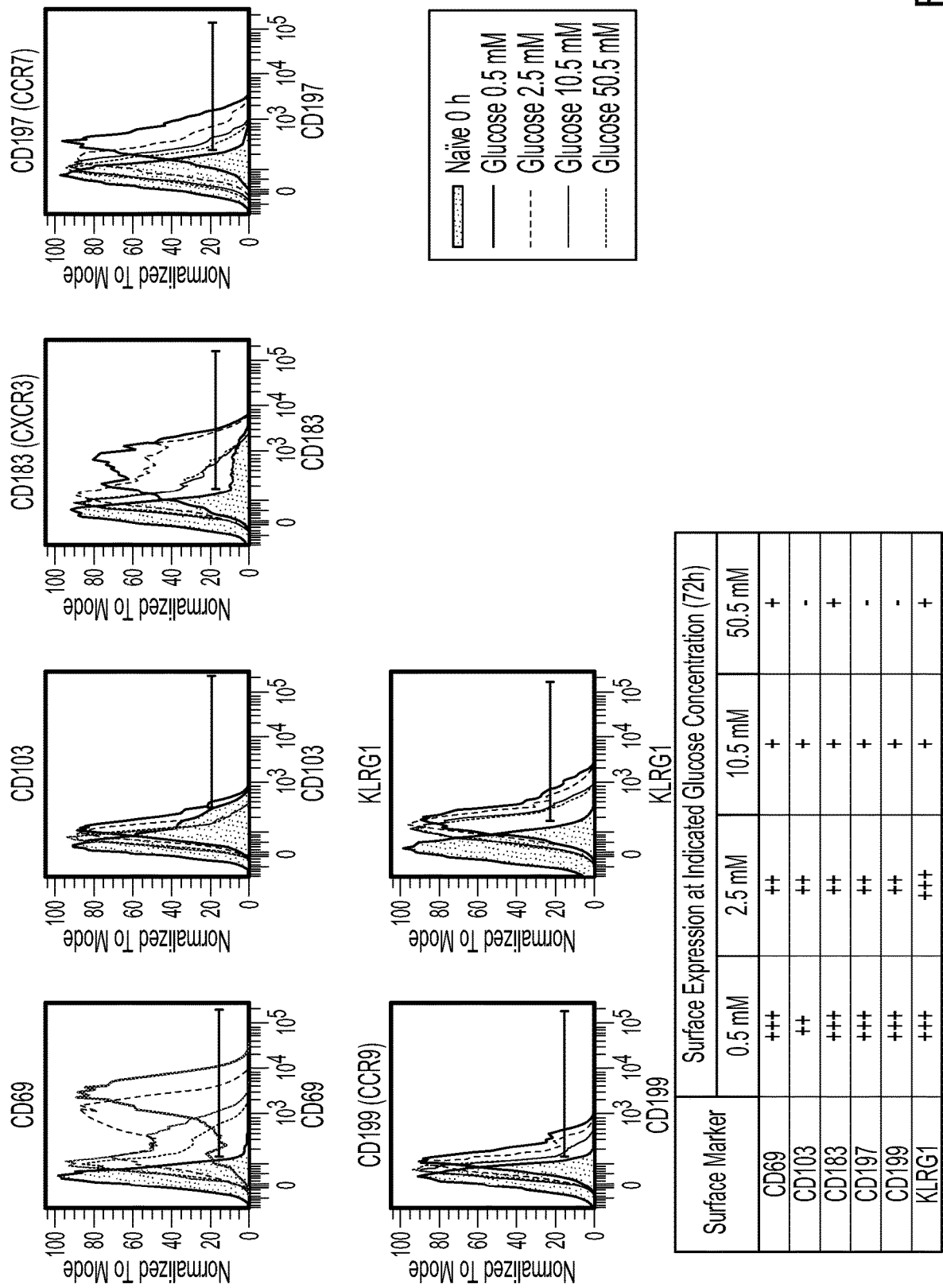
FIG. 4 contains FACS scan plots showing the effect of different glucose concentrations (0.5, 2.5, 10.5, and 50.5 mM) on the $T_{RM}$-like surface phenotype during in vitro priming of OT-1 CD8+ T cells. Naïve CD8+ T cells (time=0 hours) were used as a control.

In another experiment, the effects of different glucose concentrations during in vitro priming of OT-1 CD8$^+$ T cells on a $T_{RM}$-like surface phenotype were determined. Briefly, CD8$^+$ T cells derived from OT-1 PL Rag$^{-/-}$ TCR transgenic mice were treated as described above using either 0.5, 2.5, 10.5, or 50.5 mM of glucose, and the expression levels of CD69, CD103, CD183, CD197, CD199, and KLRG1 were assessed after 72 hours of culture. Naïve CD8$^+$ T cells (time=0 hours) were used as a control. CD8$^+$ T cells primed with antigen under a low glucose concentration (0.5 mM) expressed surface markers typical of $T_{RM}$: high CD69, CD103, CD183, CD197, CD199, and KLRG1, while CD8$^+$ T cells primed with antigen under higher amounts of glucose (e.g., 2.5, 10.5, or 50.5 mM of glucose) exhibited different structural characteristics (FIG. 4).

Figure 5:
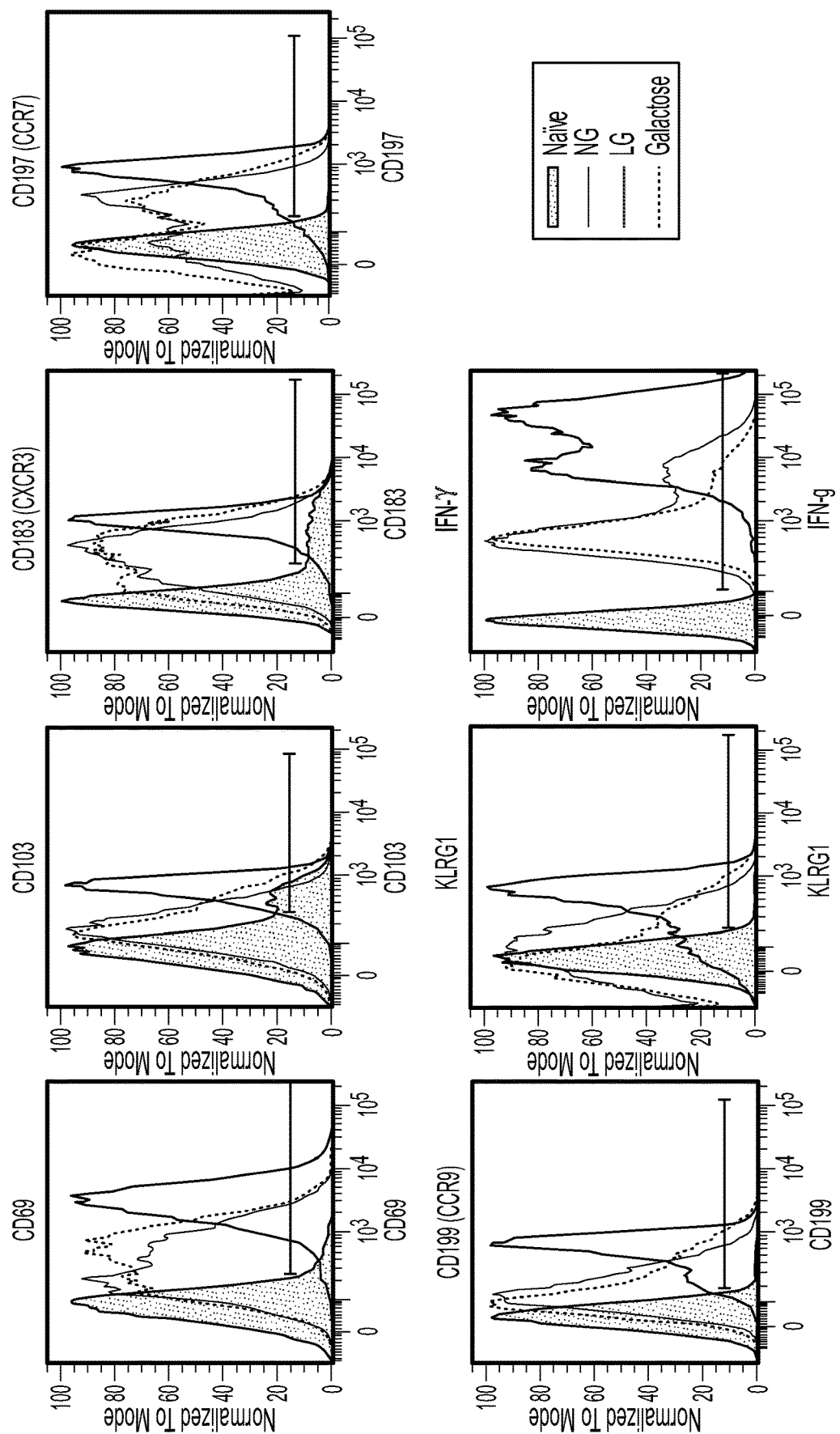
FIG. 5 contains FACS scan plots showing the effect of glucose (0.5 or 10.5 mM) or galactose (10 mM) on the $T_{RM}$-like surface phenotype during in vitro priming of OT-1 CD8+ T cells. Naïve CD8+ T cells (time=0 hours) were used as a control.

In another experiment, the effects of galactose during in vitro priming of OT-1 CD8$^+$ T cells on a $T_{RM}$-like surface phenotype were determined. Briefly, CD8$^+$ T cells derived from OT-1 PL Rag$^{-/-}$ TCR transgenic mice were treated as described above using either 0.5 mM (LG) or 10.5 mM (NG) of glucose or 10 mM of galactose, and the expression levels of CD69, CD103, CD183, CD197, CD199, KLRG1, and IFN-γ were assessed after culture. Naïve CD8$^+$ T cells (time=0 hours) were used as a control. CD8$^+$ T cells primed with antigen under a low glucose concentration (0.5 mM) expressed surface markers typical of $T_{RM}$: high CD69, CD103, CD183, CD197, CD199, KLRG1, and IFN-γ, while CD8$^+$ T cells primed with antigen under a normal glucose concentration (10.5 mM of glucose) or 10 mM of galactose exhibited different structural characteristics (FIG. 5).

In another experiment, the effects of glutamine (Gln) during in vitro priming of OT-1 CD8$^+$ T cells on a $T_{RM}$-like surface phenotype were determined. Briefly, CD8$^+$ T cells derived from OT-1 PL Rag$^{-/-}$ TCR transgenic mice were treated as described above using 0.5 mM (LG) of glucose together with 2 mM or 8 mM of Gln or 10.5 mM (NG) of glucose together with 2 mM or 8 mM of Gln, and the expression levels of CD69, CD103, CD183, CD197, CD199, and KLRG1 were assessed after culture. Naïve CD8$^+$ T cells (time=0 hours) were used as a control. In addition, CD8$^+$ T cells derived from OT-1 PL Rag$^{-/-}$ TCR transgenic mice were treated as described above using 0.5 mM (LG) of glucose together with 0 mM, 0.5 mM, 2 mM, or 8 mM of Gln or 10.5 mM (NG) of glucose together with 0 mM, 0.5 mM, 2 mM, or 8 mM of Gln, and the numbers of cells after culture were determined.

Figure 6:
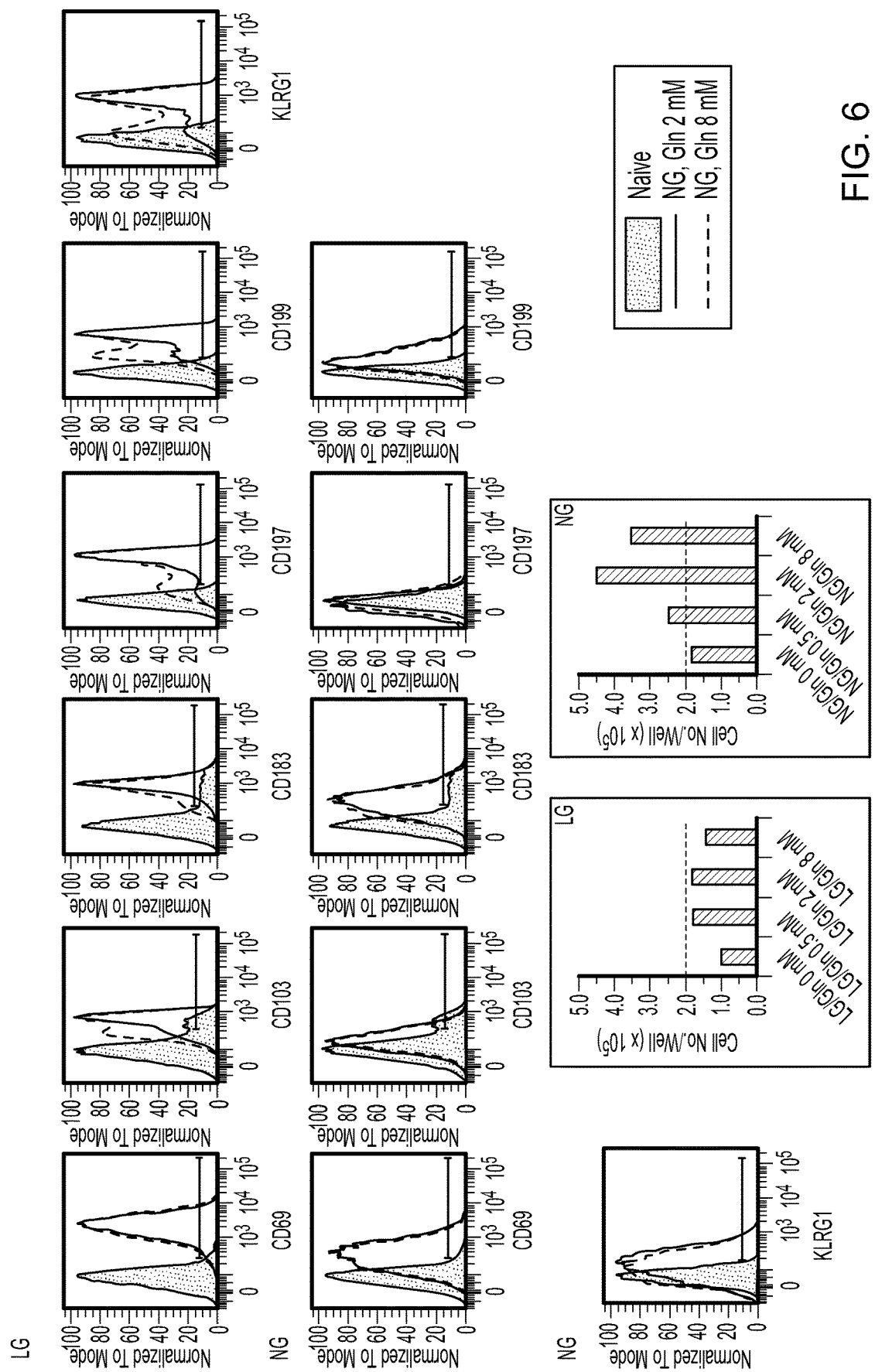
FIG. 6 contains FACS scan plots showing the effect of glucose (0.5 or 10.5 mM) together with glutamine (2 or 8 mM) on the $T_{RM}$-like surface phenotype during in vitro priming of OT-1 CD8+ T cells. Naïve CD8+ T cells (time=0 hours) were used as a control.

Glutamine concentrations regulated the CD8$^+$ T$_{RM}$ phenotype under LG conditions, but only enhanced cell recovery under NG conditions (FIG. 6).

Figure 7:
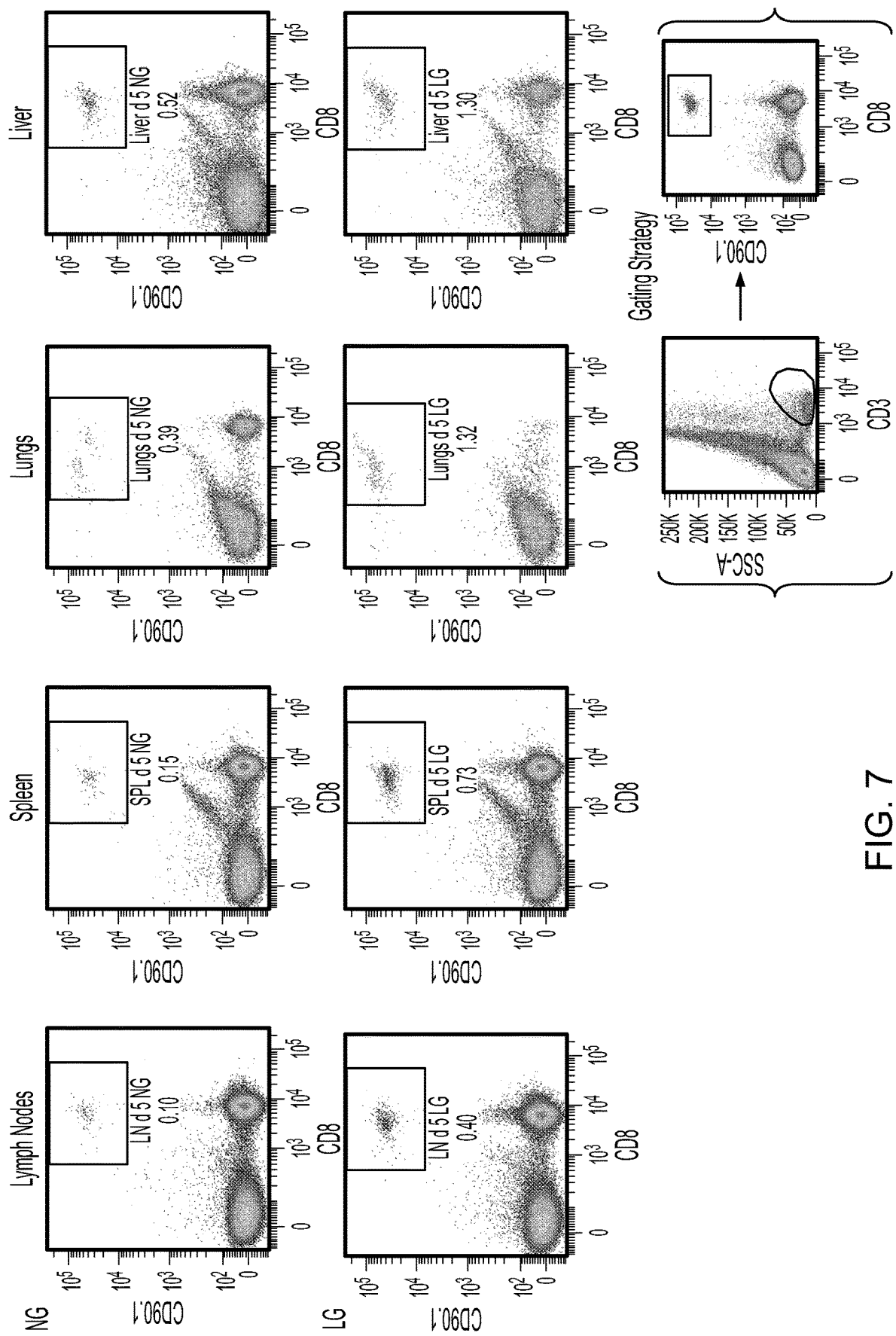
FIG. 7 contains FACS scan plots showing the homing of CD8+/CD90.1+ cells to the indicated tissues five days after injecting cells produced using 0.5 mM (LG) or 10.5 mM (NG) of glucose.
Figure 8:
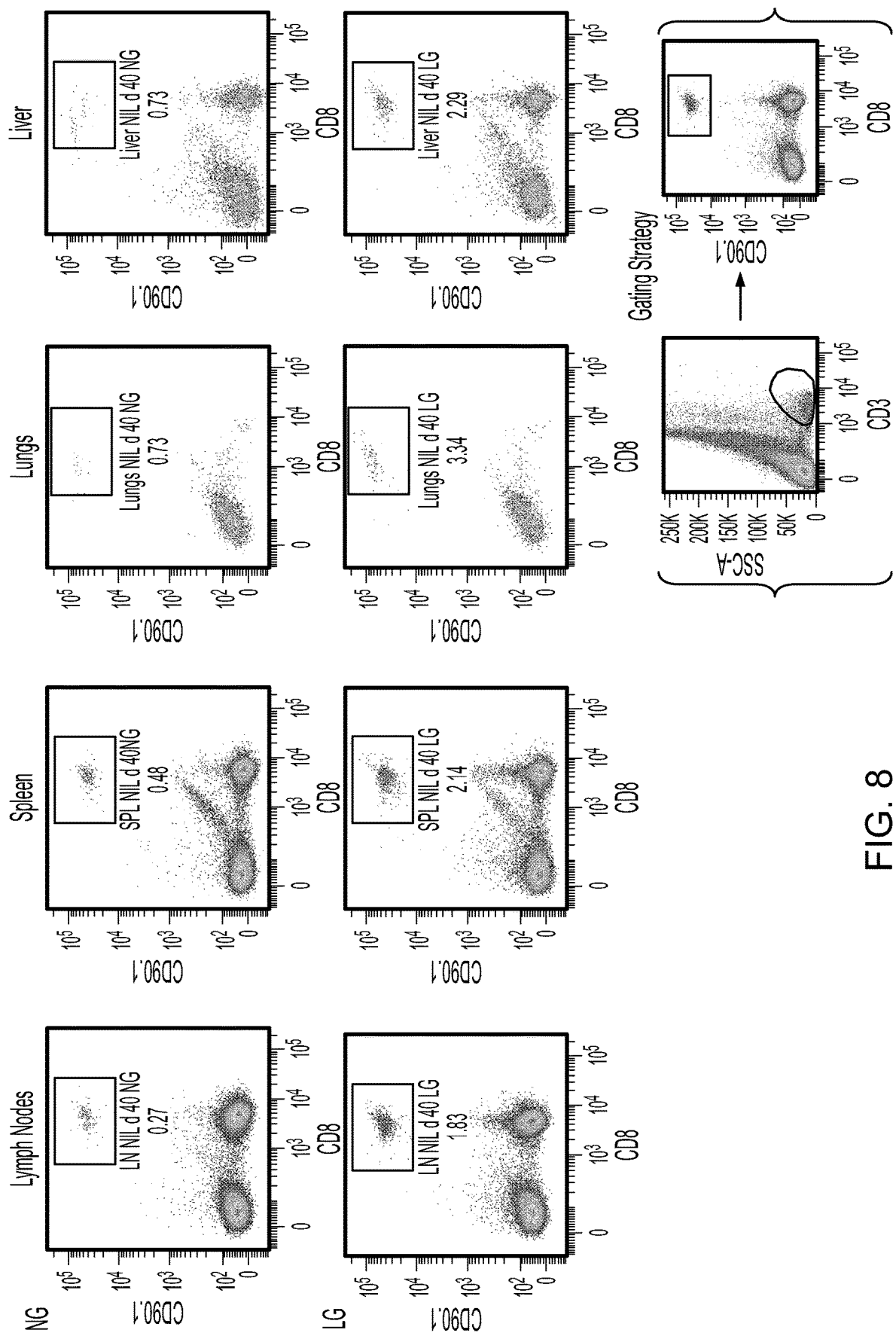
FIG. 8 contains FACS scan plots showing the homing of CD8+/CD90.1+ cells to the indicated tissues 40 days after injecting cells produced using 0.5 mM (LG) or 10.5 mM (NG) of glucose.

Example 2—T$_{RM}$ Cells Generated Using Low Concentrations of Glucose Exhibit an Increased Ability to Home to Tissues In Vivo Lymph node CD8$^+$ T cells (OT-1 PL Rag$^{-/-}$) obtained from TCR transgenic mice were obtained, stimulated, and treated as described in Example 1 using either 0.5 mM (LG) or 10.5 mM (NG) of glucose. After culture cells (T$_{RM}$ cells produced using LG and T cells produced using NG) were injected intravenously into C57BL/6 mice. Five days or 40 days later, the mice were sacrificed, and lymph node, spleen, lung, and liver tissue was harvested and evaluated by FACS for the presence of CD8$^+$ and CD90.1$^+$ T cells. Mice injected with T cells produced using LG exhibited more T cells residing in lymph node, spleen, lung, and liver tissue after five days as compared to the number of T cells residing in those tissues obtained from mice injected with T cells produced using NG (FIG. 7). In addition, mice injected with T cells produced using LG exhibited more T cells residing in lymph node, spleen, lung, and liver tissue after 40 days as compared to the number of T cells residing in those tissues obtained from mice injected with T cells produced using NG (FIG. 8).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of providing a mammal with CD8$^+$ T cells having the ability to home to tissue within said mammal comprising administering to said mammal a population of CD8$^+$ T cells produced in culture for at least 48 hours using from about 0.3 mM to about 0.7 mM glucose, wherein at least a portion of said population of CD8$^+$ T cells travel to lymph node, spleen, lung, and liver tissue within said mammal.

* * * * *